United States Patent [19]

Bowen

[11] Patent Number: 5,671,732
[45] Date of Patent: Sep. 30, 1997

[54] TRACHEOSTOMY TUBE HOLDER

[75] Inventor: Michael L. Bowen, Arlington, Tex.

[73] Assignee: Tecnol Medical Products, Inc., Fort Worth, Tex.

[21] Appl. No.: 535,327

[22] Filed: Sep. 27, 1995

[51] Int. Cl.$^6$ .................................. A61M 25/02
[52] U.S. Cl. ................... 128/207.17; 128/DIG. 15; 128/DIG. 26; 128/207.14; 128/912
[58] Field of Search .................. 128/250.26, 207.14, 128/207.15, 207.17, DIG. 26, DIG. 15, 912; 504/174, 175, 179, 180

[56] References Cited

U.S. PATENT DOCUMENTS

| | | |
|---|---|---|
| 2,765,792 | 10/1956 | Nichols ........................ 128/207.17 |
| 2,928,387 | 3/1960 | Layne ........................... 128/201.19 |
| 3,927,676 | 12/1975 | Schultz ......................... 128/DIG. 26 |
| 3,946,742 | 3/1976 | Eross ............................ 128/DIG. 26 |
| 4,088,136 | 5/1978 | Hasslinger ..................... 128/DIG. 26 |
| 4,096,863 | 6/1978 | Kaplan ......................... 128/DIG. 26 |
| 4,223,671 | 9/1980 | Muto ............................ 128/200.26 |
| 4,249,529 | 2/1981 | Nestor .......................... 128/207.17 |
| 4,313,437 | 2/1982 | Martin .......................... 128/207.17 |
| 4,326,515 | 4/1982 | Shaffer ......................... 128/207.17 |
| 4,331,143 | 5/1982 | Foster .......................... 128/207.17 |
| 4,331,144 | 5/1982 | Wapner ........................ 128/207.17 |
| 4,378,012 | 3/1983 | Brown .......................... 128/207.17 |
| 4,449,527 | 5/1984 | Hinton ......................... 128/207.17 |
| 4,483,337 | 11/1984 | Clair ............................ 128/207.17 |
| 4,485,822 | 12/1984 | O'Connor ..................... 128/207.17 |
| 4,520,813 | 6/1985 | Young .......................... 128/207.17 |
| 4,530,354 | 7/1985 | Froilan ......................... 128/207.17 |
| 4,537,192 | 8/1985 | Foster .......................... 128/207.17 |
| 4,548,200 | 10/1985 | Wapner ........................ 128/207.17 |
| 4,592,351 | 6/1986 | Smith ........................... 128/207.17 |
| 4,622,034 | 11/1986 | Shattuck ....................... 128/207.17 |
| 4,649,913 | 3/1987 | Watson ......................... 128/207.14 |
| 4,649,915 | 3/1987 | Heyden ........................ 128/207.17 |
| 4,658,814 | 4/1987 | Anderson ...................... 128/207.17 |
| 4,744,358 | 5/1988 | McGinnis ..................... 128/207.17 |
| 4,774,943 | 10/1988 | Yu ............................... 128/207.14 |
| 4,774,944 | 10/1988 | Mischinski ................... 128/207.17 |
| 4,844,061 | 7/1989 | Carroll ......................... 128/201.26 |
| 4,867,154 | 9/1989 | Potter .......................... 128/207.17 |
| 4,906,234 | 3/1990 | Voychebovski ............... 128/207.17 |
| 5,000,741 | 3/1991 | Kalt ............................. 128/DIG. 26 |
| 5,009,227 | 4/1991 | Nieuwstad .................... 128/207.17 |
| 5,010,884 | 4/1991 | Van Derdoes ................. 128/207.17 |
| 5,060,645 | 10/1991 | Russell ......................... 128/207.14 |
| 5,076,269 | 12/1991 | Austin .......................... 128/207.17 |
| 5,101,822 | 4/1992 | Kimmel ........................ 128/207.14 |
| 5,123,410 | 6/1992 | Greene ......................... 128/207.17 |
| 5,205,832 | 4/1993 | Tuman ......................... 128/912 |
| 5,230,332 | 7/1993 | Strickland .................... 128/207.14 |
| 5,237,988 | 8/1993 | McNeese ...................... 128/207.17 |
| 5,285,777 | 2/1994 | Beckwith ...................... 128/207.15 |
| 5,292,480 | 3/1994 | Zemo ........................... 128/207.17 |
| 5,305,742 | 4/1994 | Styers .......................... 128/207.17 |
| 5,306,233 | 4/1994 | Glover ......................... 128/207.17 |
| 5,320,097 | 6/1994 | Clemens ....................... 128/207.17 |
| 5,341,802 | 8/1994 | Calebaugh .................... 128/200.26 |
| 5,345,931 | 9/1994 | Battaglia, Jr. ................. 128/207.17 |
| 5,357,952 | 10/1994 | Schuster ....................... 128/207.17 |
| 5,368,024 | 11/1994 | Jones ........................... 128/207.17 |

*Primary Examiner*—Vincent Millin
*Assistant Examiner*—V. Srivastava
*Attorney, Agent, or Firm*—Baker & Botts, L.L.P.

[57] ABSTRACT

The invention relates to a tracheostomy tube holder having a strap and at least two tabs. The tabs are designed to pass through slots on the tracheostomy tube. The tabs have VELCRO type hook surfaces on their ends for releasable attachment to the exterior surface of the strap which has a soft VELCRO type loop surface. This provides for a tracheostomy tube holder which is inexpensive to make and use and which provides significant flexibility in the initial installation and subsequent replacement of individual components when they become soiled in use.

27 Claims, 1 Drawing Sheet

TRACHEOSTOMY TUBE HOLDER

TECHNICAL FIELD OF THE INVENTION

This invention relates to a holder for holding a tracheostomy tube which has been inserted in a patient's neck and into his trachea. More particularly, this holder provides an inexpensive strap and at least two tabs for releasably attaching the tracheostomy tube to the strap, such that the tabs and the strap encircle the patient's neck to hold the tracheostomy tube in place. This invention provides a tracheostomy tube holder which is much more adjustable and flexible in its operation than the prior art devices.

BACKGROUND OF THE INVENTION

Following a tracheotomy, the surgical operation of cutting into the trachea through the skin, generally a tracheostomy tube is inserted through the skin and into the trachea to keep the passage open for the passage of air, tubes, etc. into the patient's trachea and other connecting organs. Generally, the tracheostomy tube has a flange surface which extends parallel to the front portion of the patient's neck. This flange surface has two lateral slots for connecting with a strip or band to encircle the patient's neck to hold the tracheostomy tube in place.

It is desired to firmly and securely hold the tracheostomy tube in the desired position. In the past, rolls of cloth strips have been used, where a portion of the strip is cut from the roll to encircle the patient's neck. The two ends of the cloth strip are then placed through the lateral slots in the flange surface of the tracheostomy tube and tied back on itself to hold the tracheostomy tube in position. The cloth strips suffer from several disadvantages. First, they have a tendency to irritate a patient's neck. Second, as they require a knot to hold the tracheostomy tube in place, it is time-consuming and difficult to replace the strip when it becomes soiled. Additionally, the knots tied in the cloth strip may irritate the patient's neck or come undone if not tied properly, releasing the tracheostomy tube.

Tracheostomy tubes have been taped in place, however this presents an unacceptable situation as far as the patient's comfort is concerned.

U.S. Pat. No. 4,331,144 discloses a band for supporting a tracheostomy tube. While this band overcomes some of the shortcomings of cloth strips and tape, it has several shortcomings. First, in the manufacturing of this band, there are many fastening steps where certain components are fastened to other components, leading to a high manufacturing cost. Also, the band material is expensive, and thus, costly to discard and replace once it is soiled. Further, there is limited flexibility in the use of this band, as once one section of the band becomes soiled, the whole band with its fastening strips must be removed, discarded, and replaced. Not only is it expensive to replace the whole band with each attached component once a small section becomes soiled, it is also time-consuming. Still further, this band does not lend itself well to having a standard size band which may be adjustable from a child's neck up to a large adult's neck.

There exists a need for an inexpensive and disposable holder for encircling a patient's neck to firmly and securely hold a tracheostomy tube in place, where the components of the holder are easily and inexpensively replaced, such that when one component becomes soiled, only that component needs to be replaced. Also, there is a need for a strap of a standard size capable of fitting a large adult which can easily be cut to fit a small child, such that a hospital need only maintain in its inventory a "one size fits all" tracheostomy tube holder.

SUMMARY OF THE INVENTION

The invention relates to a holder for holding a tracheostomy tube in place which has two major components, a strap and at least two tabs. The strap is designed to encircle the patient's neck and has an exterior surface constructed of a soft VELCRO type loop material. The strap material is also easily cut, absorbent, inexpensive and readily disposable. The tabs have VELCRO type hook surfaces on each end and are designed to pass through slots on the tracheostomy tube and connect to the strap's exterior VELCRO type loop surface to hold the tracheostomy tube in position. Due to the VELCRO on the ends of the tabs and the strap's exterior surface being constructed of a soft loop material, the tabs are very adjustable and can easily be replaced if they become soiled.

It is an object of this invention to provide a tracheostomy tube holder which is inexpensive to manufacture and use, which is very flexible in its adjustability and that it can fit a variety of neck sizes, and which the individual components thereof can be replaced if they become soiled.

It is further an object of this invention to provide a kit for holding a tracheostomy tube in the desired position which includes a strap and three to about ten tabs such that when the tabs become soiled due to their proximity to the incision, may frequently, easily and inexpensively be removed and replaced.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF EXEMPLARY EMBODIMENTS

Figure 1:
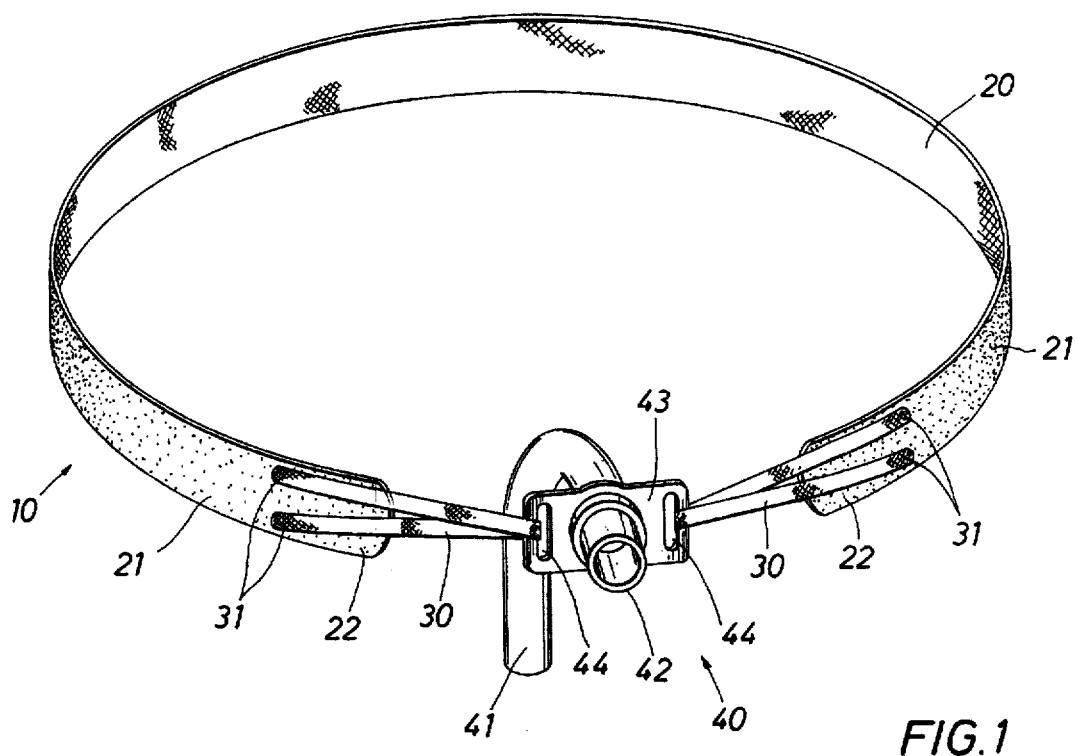
FIG. 1 is a top view of the device of the present invention.
Figure 2:
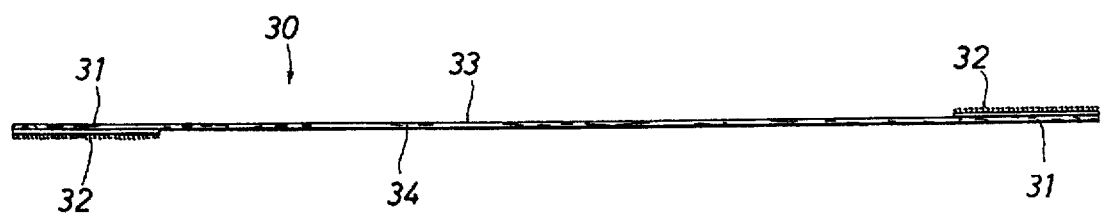
FIG. 2 is a side view of the tab of the FIG. 1 device.

The preferred embodiments of the present invention and its advantages are best understood by referring to FIGS. 1–2 of the drawings, like numerals being used for like and corresponding parts of the various drawings.

FIG. 1 shows a holder 10 which is formed of two major components, a strap 20 and at least two tabs 30.

Tracheostomy tubes 40, as available from a number of suppliers, are formed of three major components: (1) an internal tube 41 which extends into the trachea; (2) an external tube 42 which extends externally to provide external access to the trachea; and (3) a flange surface 43 which extends parallel to the front surface of the patient's neck (not shown) and has two slots 44 which provide an attachment point for the band or strip of the prior art or the holder 10 of the present invention to fasten to the tracheostomy tube 40 to hold it in place.

The strap 20 is constructed of a material which is absorbent, inexpensive and readily disposed of. Further, it is desirable that the strap 20 may be easily cut. The materials which may be used to construct the strap include cotton and paper. The strap 20 has an exterior surface 21 which is preferably constructed of a soft VELCRO type loop material. The strap 20 may be constructed of a single material having the above properties or may be constructed of two or more materials bonded together.

The strap 20 is designed and sized to substantially encircle a patient's neck, generally leaving sufficient room to fasten the tabs 30 and include the tracheostomy tube 40. The strap 20 has two opposed strap ends 22 which, in use, are placed in proximity to the tracheostomy tube flange surface 43.

As can be seen, the strap 20 may be easily and inexpensively manufactured by simply being cut or stamped from a larger piece of material having the same material(s) of construction. After cutting or stamping the strap 20, this component requires no further manufacturing steps in its construction.

The holder 10 includes at least two tabs 30. As shown in FIGS. 1 and 2, the tabs are formed in a generally elongated or rectangular shape having two opposed ends 31. Each tab is designed to pass through tracheostomy tube slot 44. Preferably, the tabs 30 have a VELCRO type hook surface 32 which is releasably attachable to the exterior loop surface 21 of the strap 20. The tabs 30 have a top surface 33 and a bottom surface 34. Preferably, a first VELCRO hook surface 32 is located on the top surface 33 of one opposed end 31 while a second VELCRO hook surface is located on the bottom surface 34 at the other opposed end 31. This placement of the VELCRO hook surfaces 32 on the tab's 30 top surface 33 and bottom surface 34 is preferred, as upon attachment through the tracheostomy tube slots 44 to the exterior surface 21 of strap 20, the tab 30 is simply folded at the slot 44 (see FIG. 1) and is not rolled, as this could irritate the patient's neck.

While VELCRO type hook and loop surfaces are the preferred releasable attachment means, the releasable attachment means may be of the adhesive type, such as the adhesive releasable attachment means included on some disposable diapers.

As can be seen, the design of the present holder 10 allows significant flexibility in placing and adjusting the holder 10 about a patient's neck. Also, it is preferred that the strap 20 be constructed of a material which may be easily cut, such that a strap 20 could be designed to fit a large adult, but if needed to fit a small child, could easily be cut without any shredding, delaminating or other undesired effects. Further, since substantially the whole exterior surface 21 of strap 20 is constructed of the soft VELCRO loop material, the VELCRO hook surfaces 32 on the tabs 30 may be easily adjusted to any of a number of positions to provide the ultimate comfort for the patient.

With an open incision in the patient's neck, frequently blood and other bodily fluids are released. With the prior art devices, once they become soiled, the whole device must be removed and discarded. This has several disadvantages. First, it is unnecessarily expensive to replace the whole device. Secondly, it is time-consuming as the nurse must totally remove the strip or band from around the patient's neck. Third, it may be inconvenient for the patient, as the patient may have to lift his head to allow the nurse access to remove the strip or band from around his neck. The present invention overcomes these disadvantages. First, since the tabs 30 are in proximity to the open incision, it is most likely that the tabs 30 will become soiled. The present invention allows individual tabs 30 to be removed, discarded and replaced. Thus, frequently the entire holder 10 need not be removed and replaced. The removal of one or both of the tabs 30 is quicker for the attending nurse, more cost effective, and more convenient for the patient, as the strap 20 need not be removed from its position encircling the patient's neck unless it itself is soiled.

The present invention provides for a kit which includes one strap 20 and at least two tabs 30. Generally, the kit includes about two to about ten tabs. Preferably, the kit contains at least three tabs 30. Most preferably, the kit includes three to about ten tabs 30. As discussed above, it is preferred to provide more than two tabs 30, because the tabs 30 are most likely to become soiled due to their proximity to the incision. As such, a kit containing extra tabs 30 will allow soiled tabs 30 to be removed, disposed and replaced with the extra tabs 30 located in the kit. It has been estimated that a total of three to about ten tabs 30 is most preferred, as this number of extra tabs 30 will generally be replaced before the strap 20 becomes sufficiently soiled to warrant its replacement. With the kit of the present invention, upon opening and using the kit for the initial installation of the holder 10 about a patient's neck, the extra tabs 30 are maintained in a package, preferably resealable, not shown, which can be located preferably in the patient's room so that the extra tabs 30 are easily accessible when needed to replace soiled tabs 30.

The strap 20 and tabs 30 are preferably designed such that the holder 10 is a "one size fits all" holder 10 which can be cut to accommodate smaller patients. To accomplish this end, it is preferable that the strap 20 be generally elongated or rectangular in shape having a length of about 12 inches to about 20 inches and a width of about 1 inch to about 2 inches. Also, the tabs 30 are generally elongated or rectangular in shape having a length of about 3 inches to about 8 inches and a width of about ¼ inch to about ½ inch. The corners of the strap 20 and the tabs 30 are preferable rounded to increase the patient's comfort.

The tracheostomy tube holder 10 solves the problems mentioned above by providing a holder 10 which provides a way of quickly and easily initially placing the holder 10 about a patient's neck and using the tabs 30 to hold the tracheostomy tube 40 in the desired position. Once the tabs 30 become soiled, they can easily be replaced, preferably with extra tabs 30 supplied in a kit with the strap 20. The holder 10 provides more flexibility over prior art devices and is more inexpensive to make and use than the prior art devices. As can be seen, the design of the present holder 10 allows manufacturing using automated techniques and substantially reduces manufacturing cost over the prior art devices.

Although the present invention and its advantages have been described in detail, it should be understood that various changes, substitutions, and alterations can be made therein without departing from the spirit and scope of the invention as defined by the appended claims.

What is claimed is:

1. A device for encircling a patient's neck and holding a tracheostomy tube which has been inserted into the patient's neck, a tracheostomy tube having first and second lateral slots formed as a pan thereof, comprising:

a strap for encircling the patient's neck having an exterior first attachment surface and two opposite ends;

at least two tabs, each tab having opposed first and second tab ends, each tab end having a second attachment surface releasably attachable to the first attachment surface on the strap;

the second attachment surface on each tab end of each tab cooperating with the first attachment surface on the strap to allow attaching and removing each respective tab from the strap;

each tab having a top surface and a bottom surface with the respective second attachment surface on the tint tab end disposed on the top surface and the respective second attachment surface on the second tab end disposed on the bottom surface; and wherein the tabs are designed to pass respectively through the first and second lateral slots and attach near the respective ends of the strap such that the strap and tabs cooperate with each other to encircle the patient's neck to hold a tracheostomy tube which has been inserted into the patient's neck.

2. The device of claim 1, wherein the first attachment surface is a loop surface and the second attachment surface is a hook surface.

3. The device of claim 1, wherein the strap is formed in part from a material which is easily cut.

4. The device of claim 1, wherein the strap is formed in part from a material which is absorbent, inexpensive and disposable.

5. The device of claim 1, wherein the tabs comprise a material which is absorbent, inexpensive and disposable.

6. The device of claim 1, wherein the strap is sized and shaped to encircle a major portion of the patient's neck.

7. The device of claim 1, wherein the strap is elongated having a length of about 12 in. to about 20 in. and a width of about 1 in. to about 2 in.

8. The device of claim 1, wherein the tabs are elongated having a length of about 3 in. to about 8 in. and a width of about ¼ in. to about ½ in.

9. A device for encircling a patient's neck and holding a tracheostomy tube which has been inserted into the patient's neck, a tracheostomy tube having two lateral slots, formed as a part thereof, comprising:

a strap having first and second ends, the first end having an exterior first attachment surface disposed adjacent thereto and the second end having an exterior second attachment surface disposed adjacent thereto;

at least two tabs for engagement with the strap such that the strap and the tabs in combination with each other encircle the patient's neck to hold the tracheostomy tube;

a first tab having two opposed tab ends with each tab end releasably attachable to the first attachment surface adjacent to the first end of the strap, each tab end further having a respective third attachment surface cooperating with the first attachment surface adjacent to the first end of the strap to allow removing the first tab from the strap, the first tab sized to pass through one of the lateral slots;

a second tab having two opposed tab ends, each tab end releasably attachable to the second attachment surface adjacent to the second end of the strap, each tab end further having a respective fourth attachment surface cooperating with the second attachment surface adjacent to the second end of the strap to allow removing the second tab from the strap, the second tab sized to pass through one of the lateral slots;

the first tab having a top surface and a bottom surface with the respective third attachment surface at one end of the first tab disposed on the top surface and the respective third attachment surface at the other end of the first tab disposed on the bottom surface;

the second tab having a top surface and a bottom surface with the respective fourth attachment surface at one end of the second tab disposed on the top surface and the respective fourth attachment surface at the other end of the second tab disposed on the bottom surface;

the third attachment surface at one end of the first tab cooperating with the third attachment surface at the other end of the first tab whereby the first tab may be releasably attached to the first attachment surface at one end of the strap with one end of the first tab spaced from the other end of the first tab on the first attachment surface at the one end of the strap; and the fourth attachment surface at one end of the second tab cooperating with the fourth attachment surface at the other end of the second tab whereby the second tab may be releasable attached to the first attachment surface at the other end of the strap with the one end of the second tab and the other end of the second tab spaced from each other on the first attachment surface at the other end of the strap.

10. The device of claim 9, wherein the first attachment surface is a loop surface and the second attachment surface is a hook surface.

11. The device of claim 9, wherein the strap is formed in part from a material which is easily cut.

12. The device of claim 9, wherein the strap is formed in part from a material which is absorbent, inexpensive and disposable.

13. The device of claim 9, wherein the tabs comprise a material which is absorbent, inexpensive and disposable.

14. The device of claim 9, wherein the strap is sized and shaped to encircle a major portion of the patient's neck.

15. The device of claim 9, wherein the strap is elongated having a length of about 12 in to about 20 in. and a width of about 1 in. to about 2 in.

16. The device of claim 9, wherein the tabs are elongated having a length of about 3 in. to about 8 in. and a width of about ¼ in. to about ½ in.

17. A tracheostomy tube holder kit having a tracheostomy tube holder for holding a tracheostomy tube in place in a patient's neck, comprising:

a strap for encircling the patient's neck, the strap having two opposite ends with an exterior first attachment surface disposed adjacent to each of the ends;

at least two tabs, each tab having two opposed tab ends, each tab end having a second attachment surface disposed adjacent thereto for releasable attaching the respective tab to the first attachment surface adjacent to one end of the strap;

each tab having a top surface and a bottom surface with the second attachment surface adjacent to one tab end disposed on the top surface and the second attachment surface adjacent to the other tab end disposed on the bottom surface; and each tab carried in the kit separate from the strap until one of the second attachment surfaces of a respective tab has been releasable attached to one of the first attachment surfaces of the strap.

18. The kit of claim 17, wherein the first attachment surface is a loop surface and the second attachment surface is a hook surface.

19. The kit of claim 17, wherein the kit comprising at least three tabs.

20. The kit of claim 17, wherein the kit contains three to about ten tabs.

21. The kit of claim 17, wherein the strap is formed in part from a material which is easily cut.

22. The kit of claim 17, wherein the strap is formed in pan from a material which is absorbent, inexpensive and disposable.

23. The kit of claim 17, wherein the tabs comprise a material which is absorbent, inexpensive and disposable.

24. The kit of claim 17, wherein the strap is sized and shaped to encircle a major portion of the patient's neck.

25. The kit of claim 17, wherein the strap is elongated having a length of about 12 in. to about 20 in. and a width of about 1 in. to about 2 in.

26. The kit of claim 17, wherein the tabs are elongated having a length of about 3 in. to about 8 in. and a width of about ¼ in. to about ½ in.

27. A tracheostomy tube holder for encircling a patient's neck and holding a tracheostomy tube having at least two slots for attachment with the tracheostomy tube holder comprising:

a strap and at least two tabs which may be releasable secured to and removed from the strap;

the strap having two opposite ends with an exterior first attachment surface disposed adjacent to each of the ends;

each tab having a first tab end and a second tab end with each tab end having a respective second attachment surface disposed adjacent thereto for releasable securing the respective tab ends of each tab to the first attachment surface adjacent to one end of the strap;

each tab having a top surface and a bottom surface with the respective second attachment surface disposed on the top surface adjacent to the first tab end and the respective second attachment surface disposed on the bottom surface adjacent to the second tab end; and the second attachment surface at the first tab end cooperating with the second attachment surface of the second tab end whereby the respective tab may be releasable attached to the first attachment surface at the one end of the strap with the respective first tab end and the respective second tab end spaced from each other on the first attachment surface at the one end of the strap.

* * * * *